US011337916B2

(12) United States Patent
Botto et al.

(10) Patent No.: US 11,337,916 B2
(45) Date of Patent: May 24, 2022

(54) *MYRCIARIA DUBIA* FRUIT EXTRACTS RICH IN ORGANIC ACIDS, COSMETIC COMPOSITIONS COMPRISING SAME AND COSMETIC USES THEREOF (71) Applicants: ISP INVESTMENTS LLC, Wilmington, DE (US); JAFER ENTERPRISES R&D, S.L., Granollers (ES)

(72) Inventors: Jean-Marie Botto, Valbonne (FR); Christophe Capallere, Nice (FR); Catherine Gondran, Callian (FR); Isabelle Imbert, Cannes (FR); Sèbastien Garnier, Le Rouret (FR); Erell Le Borgne, Antibes (FR)

(73) Assignees: ISP INVESTMENTS LLC, Wilmington, DE (US); JAFER ENTERPRISES R&D S.L.

( * ) Notice: Subject to any disclaimer, the term of this patent is extended or adjusted under 35 U.S.C. 154(b) by 43 days.

(21) Appl. No.: 16/965,511

(22) PCT Filed: Jan. 31, 2019

(86) PCT No.: PCT/EP2019/052452
§ 371 (c)(1),
(2) Date: Jul. 28, 2020

(87) PCT Pub. No.: WO2019/149864
PCT Pub. Date: Aug. 8, 2019

(65) Prior Publication Data
US 2021/0045996 A1 Feb. 18, 2021

(30) Foreign Application Priority Data
Jan. 30, 2018 (FR) ...................... 1870096

(51) Int. Cl.
*A61K 36/00* (2006.01)
*A61K 8/9789* (2017.01)
*A61Q 19/08* (2006.01)

(52) U.S. Cl.
CPC ............ *A61K 8/9789* (2017.08); *A61Q 19/08* (2013.01); *A61K 2800/82* (2013.01)

(58) Field of Classification Search
CPC ...................... A61K 2236/33; A61K 2236/333
See application file for complete search history.

(56) References Cited

U.S. PATENT DOCUMENTS

2006/0104927 A1* 5/2006 Nagamine .............. A61Q 19/02
424/62

FOREIGN PATENT DOCUMENTS

WO 2014020219 A1 2/2014
WO WO-2014020219 A1 * 2/2014 ........... A61K 8/9789

OTHER PUBLICATIONS

Alves et al, Camu-camu (*Myrciaria dubia* McVaugh): a rich natural source of vitamin C. Proceedings of the Interamerican Society for Tropical Horticulture (2002), vol. 46, pp. 11-13 (Year: 2002).*
Sergio M Zapata et al., "Camu-camuMyrciaria dubia (HBK) McVaugh: Chemical composition of fruit", Journal of the Science of Food and Agriculture, Jan. 1, 1993, pp. 349-351, vol. 61, No. 3 (Abstract only submitted).
Aline Souza et al., "Bioactive compounds in the peel of camu camu genotypes from Embrapa's active germplasm bank", Food Science and Technology, Oct. 26, 2017, pp. 67-71, vol. 38, No. 1.
Rosana Chirinos et al., "Antioxidant compounds and antioxidant capacity of Peruvian camu camu (*Myrciaria dubia* (H.B.K.) McVaugh) fruit at different maturity stages", Food Chemistry, Elsevier LTD, NL, Jun. 15, 2010, pp. 1019-1024, vol. 120, No. 4 (Abstract only submitted).
PCT, International Search Report and Written Opinion, International Application No. PCT/EP2019/052452, dated May 13, 2019 (pp. 12).
PCT, English Translation of International Search Report, International Application No. PCT/EP2019/052452, dated May 13, 2019 (pp. 3).

* cited by examiner

*Primary Examiner* — Qiuwen Mi
(74) *Attorney, Agent, or Firm* — FisherBroyles, LLP; Susan Oiler

(57) ABSTRACT

A pulp and skin extract from dried, seed-free *Myrciaria dubia* fruit. The *Myrciaria dubia* fruit has a maturity of at least 70%, a soluble solids/acidity ratio between 2.5 and 3, and it is rich in organic acids. The extract is obtained by solid-liquid extraction in a hydro-polyalcohol solvent selected from a hydro-glycerol and/or hydro-gylcolic solvent under agitation or with ultrasound. The extract is an active agent in cosmetic compositions, which reduce the signs of skin fatigue.

8 Claims, 4 Drawing Sheets

FIGURE 2

\* highly significant after student's t test n=3

Normal reconstructed epidermis

"Tired" reconstructed epidermis

"Tired" reconstructed epidermis + 0.1% E1 Myrciaria extract

MYRCIARIA DUBIA FRUIT EXTRACTS RICH IN ORGANIC ACIDS, COSMETIC COMPOSITIONS COMPRISING SAME AND COSMETIC USES THEREOF

CROSS-REFERENCE TO RELATED APPLICATIONS

The present invention is filed under 35 U.S.C. § 371 as the U.S. national phase of International Patent Application No. PCT/EP2019/052452, filed Jan. 31, 2019, which designated the United States and which claims the benefit of French Patent Application No. 1870096 filed Jan. 30, 2018, which is hereby incorporated in its entirety including all tables, figures, and claims.

The invention relates to a *Myrciaria dubia* (Camu-camu) fruit extract rich in organic acids, preparation process for same, cosmetic compositions comprising same, and cosmetic uses thereof.

The Camu-camu (*Myrciaria dubia* (H.B.K.) Mc Vaugh.) is a shrub native to the Amazon basin belonging to the Myrtaceae family. This shrub of about 3 metres high grows in the Amazonian forest of Peru, Colombia, Venezuela and Brazil in the floodplains, lakes and rivers of most of the Amazon. This highly-branched shrub flowers from November to December and August to September, and bears fruit from January to March and October to November.

The fruits of Camu-camu are round berries of dark red-purple colour measuring 1 to 3 cm in diameter with a fine, smooth, shiny skin and fleshy, acidic pulp. The ripe berries are traditionally picked by hand directly by canoe during the flood periods of the rainy season in the Amazonian swamp areas. For several years now, plantations have been established in a number of Amazonian countries. Indigenous peoples have been using Camu-camu for medicinal purposes for over 700 years to treat infections, reduce pain, strengthen joints, maintain longevity, strengthen the immune and nervous systems, and facilitate the absorption of nutrients. Due to its natural acidity, the pulp of this nutritious fruit is primarily consumed after processing into juices, alcoholic beverages, vinegars, concentrates, jams, ice cream and cakes. The pulp accounts for between 50 and 55% of the weight of the fruit, the rest being seeds (1 to 3 seeds per fruit) and skin. Globally, Camu-camu fruit gained popularity when researchers discovered its unique nutritional and health benefits due mainly to its high natural content of vitamin C (ascorbic acid) and flavonoids. The Camu-camu fruit is known to the man of art as belonging to the "superfruits" group due to its high content of ascorbic acid or vitamin C (between 3.5% and 9% of the dry weight), multiple polyphenols, such as flavonoids (myricetin, proanthocyanidin, ellagic acid, etc.), tannins (ellagitannin, mainly present in the seeds) or anthocyanins, as well as terpene compounds (alpha-pinene, limonene, carotenoid, etc.), which give it strong antioxidant powers (protection against oxidative stress caused by free radicals) and other health benefits. Thanks to several of these active elements, it is also believed to play an anti-inflammatory role, strengthen the immune system and improve the body's natural defences. It is indicated as an adjuvant in case of convalescence, fatigue, flu or other viral diseases.

It is known[1-4] that the seeds of the Camu-camu fruit contain betulinic acid (triterpene), polyphenolic compounds (myricetin and derivatives, ellagic acid and derivatives, ellagitannins, proanthocyanidins) and acylphloroglucinols (isomyrtucommulone B, myrciarone B). It is also known[1,3-6] that the skin of the Camu-camu fruit contains polyphenolic compounds (myricetin and derivatives, ellagic acid and derivatives, ellagitannins, proanthocyanidins), cyanidine-3-glucoside, delphinidine-3-glucoside), carotenoids (all-trans lutein, beta-carotene, violaxanthin, luteoxanthin) and acylphloroglucinols (myrciarone A, rhodomyrtone). Lastly, it is known[4,7-9] that the pulp of the Camu-camu fruit contains polyphenolic compounds (myricetin and derivatives, ellagic acid and derivatives, ellagitannins, cyanidine-3-glucoside, quercetin and derivatives), ascorbic acid and dehydroascorbic acid, fatty acids (stearic acid, linoleic acid, oleic acid, gamma and alpha-linolenic acid, tricosanoic acid, eicosadienoic acid), citric acid, malic acid and isocitric acid, simple carbohydrates (mainly glucose and fructose), amino acids (serine, leucine, valine, but also glutamate, 4-aminobutanoate, proline, phenylalanine, threonine, alanine) and minerals (potassium, calcium, magnesium, sodium, phosphate, sulphate, aluminium, boron, copper, manganese, zinc). The document by Fracassetti et al.[4] has also demonstrated the presence of vitamin C and polyphenols in an extract obtained from a mixture of seeds and skin, or pulp, with a solvent 50% methanol-water and 1% formic acid, and the amounts obtained of vitamin C and polyphenols are expressed in relation to the whole plant.

The concentration of the different ingredients of the Camu-camu fruit specified above has been studied at different stages of maturity of the fruit, either from fresh or dry plant material. Zapata et al.[9] studied the chemical composition of fresh pulp at three different stages of ripeness. They showed that the vitamin C content increased by about 12% between green and ripe fruit and that the sugar content (glucose and fructose) doubled. The amino acid content also increases during fruit ripening, mainly the content of serine, valine and leucine. In this study, it was also shown that the citric acid content decreased during ripening, in contrast to malic acid, whose content increased. Isocitric acid is believed to be present in trace amounts in the pulp of this fruit. Finally, this study also showed an increase in potassium and phosphate content, a net reduction of 50-60% in sodium and sulphate content and a constant calcium and magnesium content during ripening.

Of the documents cited above, only documents 1 and 4 describe the use of the dried fruit of Camu-camu, often with the seeds, to carry out ingredient analyses. These two documents, using different analytical methods and different solvents, show that the extracts have high levels of polyphenols.

Furthermore, the document published under the number WO2014020219 discloses antioxidant compositions of a product obtained from the fruit of Camu-camu. It relates more particularly to a process for obtaining an extract of the Camu-camu fruit in a state of ripeness of between 20 and 30% and having a soluble solids/acidity ratio of between 1.40 and 2.30, said process comprising the steps of removing the seeds from the selected fruits and drying the seed-free fruits at a temperature below 60° C. The water-soluble compounds are extracted with water at acidic pH (tricarboxylic acid), and the extract has been shown to contain large amounts of vitamin C and polyphenols, including proanthocyanidins. These extracts are described for the preparation mainly of nourishing food compositions and stimulating pharmaceutical compositions; cosmetic compositions that are nourishing a priori are generally cited.

The document published under the number WO2004074304 also discloses a glycosylated derivative compound of gallic acid (1-[1,5-dihydroxy-2,2,4,4-tetramethyl-3-[[6-O-(3,4,5-trihydroxybenzoyl)-β-D-glucopyranosyl]oxy]cyclopentyl]-3-methyl-2-buten-1-one) named "CA1" derived, according to example 1, from Camu-camu seeds and having a powerful antioxidant activity and a stable whitening effect. The extraction process is carried out with methanol, a mono-alcoholic solvent, on Camu-camu seeds. According to this document, the compound CA1 is also present in the pulp and skin, but seemingly at different concentrations.

Lastly, an extract from Camu-camu also showing bleaching activity is known from the document published under number JP3431383. The extract is obtained from the whole fruit of Camu-camu, preferably fresh, by maceration with water, an organic solvent or mixture of same, for a period of at least two days. The only example in this document indicates using a maceration of the fruit with ethanol for three days.

Thus, depending on the part of the *Myrciaria dubia* fruit used, the quality of the fruit (fresh or dried) and the extraction process used, in particular the choice of solvent, the extracted molecules prove to be different in quality and quantity. However, the composition of the extract conditions the biological activity and consequently the cosmetic effectiveness. As a result, the Applicants wished to obtain a new *Myrciaria dubia* extract rich in organic acids and low in polyphenols.

The Applicants have demonstrated that an extract of skin and pulp of dried *Myrciaria dubia* fruit with a ripeness of at least 70% and free of seeds has an activity reducing signs of skin fatigue. The extract according to the invention is rich in organic acids (mixture of ascorbic acid, dehydroascorbic acid, malic acid and citric acid), and comprises minerals and sugars (fructose, glucose, sucrose and traces of maltose) and includes traces of depigmenting compounds and phenolic compounds in small quantities.

The invention thus firstly relates to pulp and skin extract of dried, seed-free *Myrciaria dubia* fruit, the ripeness of which is at least 70% and the ratio of soluble solids/acidity of which is between 2.5 and 3, said extract being rich in organic acids.

The invention secondly relates to a process for obtaining an extract according to the invention, comprising the following steps in which:
a) the pulp and skin of the seed-free dried fruit of *Myrciaria dubia*, having a ripeness of at least 70% and a soluble solids/acidity ratio of 2.5 to 3, are dispersed and extracted in a hydro-polyalcohol solvent,
b) the liquid phase loaded with compounds of interest is separated from the solid phase by decantation and/or centrifugation and/or clarifying filtration of the extract obtained from step a),
c) the liquid extract obtained in step b) is microfiltered to remove solid plant particles,
d) optionally, the liquid extract obtained in step c) is purified by filtration, ultrafiltration and/or nanofiltration,
e) optionally, the liquid *Myrciaria dubia* extract obtained for example by spraying, freeze-drying or zeodration can be dried to obtain a solid *Myrciaria dubia* extract, optionally with a drying support such as maltodextrin.

The invention also relates to a pulp and skin extract of *Myrciaria dubia* obtained directly by the process.

The invention thirdly relates to a cosmetic composition comprising, as active agent, an effective amount of a pulp and skin extract of dried *Myrciaria dubia* fruit according to the invention, and a physiologically acceptable medium.

Lastly, the invention relates fourthly to the cosmetic use of a composition according to the invention to reduce the signs of skin fatigue.

In this description, unless otherwise specified, it is understood that when a range is given it includes the upper and lower bounds of that range.

Unless otherwise stated, percentages are percentages by weight.

In the present invention:
"Hydro-polyalcohol" means a mixture of water and polyols, the latter comprising at least two alcohol radicals, more specifically from 2 to 9 alcohol radicals and from 3 to 12 carbon atoms.

"Extract rich in organic acids" means an extract containing a quantity of organic acids (mixture of total ascorbic acid, including ascorbic acid and dehydroascorbic acid, malic acid and citric acid) greater than the other ingredients identified, i.e. between 13.5% and 80.5% in relation to the dry matter of the total extract.

"Effective quantity" means the quantity of compounds of interest necessary to obtain the desired result, namely to reduce the signs of skin fatigue.

"Reduction of the signs of skin fatigue" means one, more, or all of the following signs: the presence of puffiness and dark circles under the eyes, dull complexion, dry skin, accentuation of fine lines and wrinkles such as forehead or crow's feet wrinkles, accentuation of skin slackening, an increase in the fragility of the nails and a receding of the hair line, which can appear in a healthy person. At the molecular and cellular level, skin fatigue is characterised by, amongst other things, mitochondrial dysfunction, decreased ATP production, decreased glycolysis, and decreased creatine kinase system.

The plant names Camu-camu and *Myrciaria dubia* are used interchangeably in the application.

"Topical application" means applying or spreading a composition containing the *Myrciaria dubia* extract according to the invention on the surface of the skin, a mucous membrane, or appendages.

"Physiologically acceptable" means that the compositions comprising the *Myrciaria dubia* extract according to the invention are suitable for contact with the skin or a mucous membrane without causing toxicity, intolerance or allergy reactions. In the case of compositions which can be ingested or injected into the skin, these do not exhibit toxicity, incompatibility, instability, and do not cause a systemic allergic response.

"Dry matter", expressed as a percentage by mass, means the dry residue obtained after total removal of the solvent by drying or evaporation.

"Compounds of interest" means the compounds extracted by the process according to the invention and useful in a cosmetic composition for reducing signs of skin fatigue.

"Soluble solids/acidity ratio" means the ratio of soluble solids contained in the fruit, mainly sugars, to the acidity of the fruit. During the fruit ripening process, the acids are broken down, the sugar content increases, and the total soluble solids/acidity ratio, called Brix/acidity, reaches a higher value. This ratio has no unit and corresponds to the Brix/acidity ratio calculated on the basis of the concentration of citric acid. The reference can be found for the calculation of this ratio in the document "Quality assurance in Tropical Fruit Processing" by A. Askar and H. Treptow, published in 1993 by Springer Verlag Berlin Heidelberg, page 25 paragraph 2.7.

"Ripeness of at least 70%" means that each fruit has a colour of at least 70% red and 30% green. This ripeness may be up to 100%.

"Trace compounds" means compounds whose presence is detectable but not quantifiable by routine laboratory detection methods.

The applicant filed an application for access to the genetic resource *Myrciaria dubia* (Kunth) McVau with the Peruvian Government (INIA: Instituto Nacional de Innovacion Agraria ("National Institute of Agricultural Innovation") in accordance with Andean Law, Decision No. 391, relating to the Common Regime on Access to Genetic Resources.

The invention firstly relates a pulp and skin extract of dried, seed-free *Myrciaria dubia* fruit, the ripeness of which is at least 70% the ratio of soluble solids/acidity of which is between 2.5 and 3, said extract being rich in organic acids.

The invention also relates to a pulp and skin extract of dried, seed-free *Myrciaria dubia* fruit, the ripeness of which is at least 70% and the ratio of soluble solids to acidity of which is between 2.5 and 3, obtained directly by the process described as the second subject of the invention.

In the context of the present invention, the plant part selected is the fruit of *Myrciaria dubia*, from the group consisting of the skin and pulp of the dried fruit, the seeds having been removed. The fruits are harvested when they have reached a ripeness of 70% or more of red fruit and the ratio of soluble solids/acidity is between 2.5 and 3.

In a very preferential embodiment, the extract is obtained from the pulp and skin of dried *Myrciaria dubia* fruit by solid-liquid extraction in a hydro-polyalcohol solvent selected from a hydro-glycerol and/or hydro-glycolic solvent, under conventional agitation or with ultrasound.

The extract is obtained by solid-liquid extraction of the pulp and skin of dried and crushed *Myrciaria dubia* fruit in a hydro-polyalcohol solvent selected from the group consisting of water and polyalcohols, such as glycerol, glycols such as 1,3-propanediol, and mixtures thereof. The solvent 1,3-propanediol is the preferred solvent as this solvent is agro-based.

The extraction solvent is preferably a hydro-glycerol and/or hydro-glycolic solvent, advantageously in a proportion between 30 and 90% glycerol and/or glycol in water, such as a mixture of water and 1,3-propanediol.

In an even more preferential embodiment, the extract is obtained from the pulp and skin of dried, seed-free *Myrciaria dubia* fruit by solid-liquid extraction in a hydro-polyalcohol solvent consisting of 60% 1,3-propanediol and 40% demineralised water.

Lastly, in another very preferential embodiment, the extract comprises, in relation to the dry matter of the total extract, between 13.5% and 80.5% organic acids, including malic, citric and ascorbic acids; between 4.0% and 22.0% total sugars, including in particular glucose, fructose, sucrose and maltose; and between 0.5% and 3% minerals, including potassium, magnesium, calcium, sodium, manganese, zinc and iron.

The extract according to the invention contains only traces of proteins, traces of amino acids and peptides, an amount of polyphenols between 0.08% and 2.00%, and finally traces of the depigmenting compound CAL to make reference to the extracts known from the prior art.

The invention relates secondly to a process for obtaining an extract according to the invention, comprising the following steps in which:
a) the pulp and skin of the seed-free dried fruit of *Myrciaria dubia*, having a ripeness of at least 70% and a soluble solids/acidity ratio of 2.5 to 3, are dispersed and extracted in a hydro-polyalcohol solvent;
b) the liquid phase loaded with compounds of interest is separated from the solid phase by decantation and/or centrifugation and/or clarifying filtration of the extract obtained from step a),
c) the liquid extract obtained in step b) is microfiltered to remove solid plant particles,
d) optionally, the liquid extract obtained in step c) is purified by filtration, ultrafiltration and/or nanofiltration,
e) optionally, the liquid *Myrciaria dubia* extract obtained for example by spraying, freeze-drying or zeodration can be dried to obtain a solid *Myrciaria dubia* extract, optionally with a drying support such as maltodextrin.

To carry out the process of the present invention, the plant part selected is the fruit of *Myrciaria dubia*, from the group consisting of the dried pulp and skin of the fruit, and the seeds are removed to avoid extracting lipids which would compromise the extraction of the compounds of interest.

The fruits are harvested when they have reached a ripeness of 70% or more of red fruit and the ratio of soluble solids/acidity is between 2.5 and 3.

Particularly advantageously, step (a) is carried out on the dried and crushed pulp and skin of the seed-free *Myrciaria dubia* fruit. The harvested fruit is sorted, disinfected, washed and deseeded before being dehydrated with hot air and then the dry skin and pulp are crushed.

The extract is obtained by solid-liquid extraction of the dried and ground pulp and skin of *Myrciaria dubia* fruit in a hydro-polyalcohol solvent selected from the group consisting of water and polyalcohols, such as glycerol, glycols such as 1,3-propanediol, and mixtures thereof. The solvent 1,3-propanediol is the preferred solvent as this solvent is agro-based.

Advantageously, the hydro-polyalcohol solvent is a mixture comprising from 10% to 90% by weight of glycerol and/or 1,3-propanediol in demineralised water in relation to the total weight of solvent plus water.

Further preferably, the hydro-polyalcohol solvent is a mixture comprising from 50% to 80% by weight of glycerol and/or 1,3-propanediol in demineralised water in relation to the total weight of solvent plus water.

More particularly, within the scope of the solid-liquid extraction of the pulp and skin of the deseeded and dried fruit of *Myrciaria dubia*, between 0.1 and 20% by weight (dry matter) of part of the pulp and skin of the fruit is introduced into the extraction solvent, and preferably between 1 and 15% by weight, typically between 5 and 10% by weight (the % being expressed as the weight of the dry matter in relation to the total weight used).

When the solvent used is glycerol, a proportion between 30 and 90% of glycerol in water is chosen, and advantageously between 50 and 80% (the percentages are expressed as weight of glycerol in relation to the total weight of water+glycerol).

When the solvent used is glycol and more particularly 1,3-propanediol, a proportion of between 10 and 90% of 1,3-propanediol in water is chosen, advantageously between 50 and 70% and even more advantageously a proportion of 60% of 1,3-propanediol and 40% of demineralised water is chosen (the % are expressed as the weight of 1,3-propanediol in relation to the total weight of water plus 1,3-propanediol).

The extraction temperature is advantageously between 4° C. and 100° C., and preferably between 10° C. and 80° C., and more particularly between 20° C. and 50° C.

Heating can be provided by circulating a thermal fluid in a double jacketed extraction vessel or by microwave.

The extraction time advantageously varies from 10 minutes to 4 hours, and preferably from 30 minutes to 3 hours, and even more advantageously from 1 to 2 hours.

Extraction can be carried out advantageously under vacuum, at atmospheric pressure or under pressure, preferably at atmospheric pressure or under pressure, more advantageously at atmospheric pressure.

Extraction is always carried out under stirring, thus allowing dispersion and homogenisation of the solid in the liquid, effectively improving the diffusion of the solute in the solvent.

Following the extraction of step a), the residual plant material depleted in compounds of interest is advantageously separated from the liquid phase according to step b), for example by decantation, centrifugation or clarifying filtration. The resulting liquid phase can be micro-filtered according to step c) using filter media of suitable porosity to obtain a clear solution purified of solid plant particles.

These initial liquid-solid separation steps may be followed by purification steps according to step d), for example by filtration, ultrafiltration and/or nanofiltration, to concentrate the compounds of interest at the expense of other compounds.

Thus, in a preferential embodiment of the process according to the invention, the temperature of step a) is between 4° C. and 100° C., the extraction time varies from 10 minutes to 4 hours, and the extraction is carried out under conventional stirring or with ultrasound.

The invention also relates to an extract of *Myrciaria dubia* pulp and skin obtained directly by the process.

The invention also relates to a *Myrciaria dubia* extract comprising, in relation to the dry matter of the total extract, between 13.5% and 80.5% of organic acids, including malic, citric and ascorbic acids; between 4.0% and 22.0% of total sugars, including glucose, fructose, sucrose and maltose; between 0.5% and 3% of minerals, including potassium, magnesium, calcium, sodium, manganese, zinc and iron, obtained directly by the above process.

The invention also relates to *Myrciaria dubia* extract as described in the preceding paragraph and further comprising traces of proteins, traces of amino acids and peptides, and a quantity of polyphenols between 0.08 and 2% obtained directly by the above process.

The invention relates thirdly to a cosmetic composition, comprising an extract of the pulp and skin of the fruit of *Myrciaria dubia* according to the invention, and a physiologically acceptable medium.

In a preferential embodiment according to the invention, the hydro-polyalcohol extract of the pulp and skin of the fruit of *Myrciaria dubia* is present in the composition at a concentration of 0.1 to 3% relative to the total weight of the composition, preferably 0.1 to 1.5%.

In another preferred embodiment, the compositions according to the invention are intended more particularly for topical administration. These compositions must therefore contain a physiologically acceptable medium, i.e. compatible with the skin and the appendages, and must cover all cosmetic forms. These compositions may in particular be in the form of creams, oil-in-water or water-in-oil emulsions or multiple emulsions, solutions, suspensions, gels, milks, lotions, sticks or powders, suitable for application to the skin, lips and/or appendages. These compositions include the excipients necessary for their formulation, such as solvents, thickeners, diluents, surfactants, antioxidants, dyes, preservatives, and perfumes. They can be used as a skincare product and/or as a make-up product for the skin.

The compositions according to the invention furthermore include any additive commonly used in the envisaged field of application as well as the adjuvants necessary for their formulation, such as solvents, thickeners, diluents, antioxidants, dyes, sunscreens, self-tanning agents, pigments, fillers, preservatives, perfumes, odour absorbers, cosmetic or pharmaceutical active ingredients, essential oils, vitamins, essential fatty acids, surfactants, film-forming polymers, etc.

The INCI Dictionary & Handbook ("International Nomenclature of Cosmetic Ingredients" 13th Ed. 2010) published by "the Personal Care Products Council, Inc.", Washington, D.C., describes a wide variety, without limitation, of cosmetic and pharmaceutical ingredients commonly used in the skincare industry which are suitable for use as additional ingredients in compositions according to the present invention.

Non-limiting examples of these additional ingredient classes include: healing agents, anti-ageing agents, anti-wrinkle agents, anti-atrophy agents, moisturising agents, softening agents, antibacterial agents, anti-parasitic agents, antifungal agents, fungicidal agents, fungistatic agents, bactericidal agents, bacteriostatic agents, antimicrobial agents, anti-inflammatory agents, anti-pruritic agents, anaesthetic agents, antiviral agents, keratolytic agents, anti-free radical agents, anti-seborrhoeic agents, anti-dandruff agents, agents modulating skin differentiation, proliferation or pigmentation agents, penetration accelerating agents, peeling agents, agents stimulating or inhibiting melanin synthesis, whitening, depigmenting or lightening agents, pro-pigmenting agents, self-tanning agents, NO-synthase inhibiting agents, antioxidant agents, free radical scavengers and/or anti-air pollution agents, anti-glycation agents, firming agents, agents stimulating the synthesis of dermal or epidermal macromolecules and/or agents capable of preventing or inhibiting their degradation, agents stimulating collagen synthesis, agents stimulating elastin synthesis, agents stimulating decorin synthesis, agents stimulating laminin synthesis, agents stimulating defensin synthesis, agents stimulating chaperone synthesis, agents stimulating aquaporin synthesis, agents stimulating hyaluronic acid synthesis, agents stimulating the synthesis of lipids and stratum corneum components (ceramides, fatty acids, etc.), agents inhibiting collagen degradation, agents inhibiting elastin degradation, agents stimulating fibroblast proliferation, agents stimulating keratinocyte proliferation, agents stimulating adipocyte proliferation, agents stimulating melanocyte proliferation, agents stimulating keratinocyte differentiation, agents stimulating adipocyte differentiation, acetylcholinesterase inhibiting agents, agents stimulating glycosaminoglycan synthesis, DNA repair agents, DNA protecting agents, anti-itching agents, agents for the treatment and/or care of sensitive skin, firming agents, anti-stretch mark agents, astringent agents, agents regulating sebum production, dermo-relaxing agents, healing adjuvant agents, agents stimulating re-epithelialisation, cytokine growth factors, calming agents, anti-inflammatory agents, agents acting on capillary circulation and/or microcirculation, agents stimulating angiogenesis, agents inhibiting vascular permeability, agents acting on cell metabolism, agents for improving the dermal-epidermal junction, agents for inducing head and/or body hair growth, agents for inhibiting or slowing down head and/or body hair growth, muscle relaxants, anti-pollution and/or anti-radical agents, agents for stimulating lipolysis, slimming agents, anti-cellulite agents, agents acting on the microcirculation, agents acting on cell metabolism, cleansing agents, hair styling agents, head hair growth stimulants, sunscreens, sunblocks, make-up agents, detergents, pharmaceutical products, emulsifying agents, emollients, organic solvents, antiseptic agents, deodorant active ingredients, physiologically acceptable media, surfactants, abrasive agents, absorbents, cosmetic components such as perfumes, pigments, dyes, colorants and natural colorants, essential oils, touching agents, cosmetic astringents, anti-acne agents, anti-coagulation agents, anti-foaming agents, antioxidants, ligands, biological additives, enzymes, enzyme inhibitors, enzyme inducers, coenzymes, chelating agents, plant extracts and plant derivatives, essential oils, marine extracts, agents from a biofermentation and/or biotechnology process, mineral salts, cell extracts, sunscreens (organic or mineral sunscreen agents which are active against ultra-violet A and/or B rays), ceramides, peptides, buffers, volume agents, chelating agents, chemical additives, colorants, cosmetic biocides, denaturants, medicinal astringents, external analgesics, film-forming agents, such as polymers, to exacerbate the film-forming properties and substantivity of the composition, quaternary derivatives, substantivity enhancing agents, opacifying agents, pH adjusters and regulators (e.g., triethanolamine), propellants, reducing agents, sequestering agents, skin bleaching and/or skin lightening agents, skin conditioning agents (i.e., humectants, including miscellanea and occlusives), moisture-retaining substances, alpha hydroxy acids, beta hydroxy acids, moisturisers, epidermal hydrolytic enzymes, soothing and/or healing agents, skin treatment agents, anti-wrinkle agents, agents capable of reducing or treating puffiness under the eyes, exfoliating agents, thickeners, softeners, gelling polymers, vitamins and their derivatives, wetting agents, peeling agents, calming agents, skin healing agents, lignans, preservatives (i.e. phenoxyethanol and parabens), anti-UV agents, cytotoxic agents, anti-neoplastic agents, viscosity modifiers, non-volatile solvents, pearling agents, antiperspirants, depilatories, vaccines, perfumed water, skin restructuring agents, excipients, fillers, minerals, anti-mycobacterial agents, anti-allergenic agents, Hl or H2 antihistamines, anti-irritants, agents stimulating the immune system, agents inhibiting the immune system, insect repellents, lubricants, pigments or colorants, hypopigmenting agents, photostabilisers, and mixtures thereof, as long as they are physically and chemically compatible with the other ingredients of the composition and especially with the active ingredients of the present invention.

Furthermore, the nature of these additional ingredients must not unacceptably alter the benefits of the active ingredients of the invention. These additional ingredients may be synthetic or natural, such as plant extracts, or from a biofermentation process. Additional examples can be found in the INCI Dictionary & Handbook.

Such additional ingredients may be selected from the group comprising: amino sugars, glucosamine, D-glucosamine, N-acetyl-glucosamine, N-acetyl-D-glucosamine, mannosamine, N-acetyl mannosamine, galactosamine, N-acetyl galactosamine, vitamin B3 and derivatives thereof, niacinamide, sodium dehydroacetate, dehydroacetic acid and its salts, phytosterols, salicylic acid compounds, hexamidines, dialkanoyl dihydroxyproline compounds, extracts and derivatives of soya, equol, isoflavones, flavonoids, phytantriol, farnesol, geraniol, bisabolol, peptides and derivatives thereof, di-, tri-, tetra-, penta-, and hexapeptides and derivatives thereof, lys-thr-thr-lys-ser, palmitoyl-lys-thr-thr-lys-ser, carnosine, N-acyl amino acid compounds, retinoids, retinyl propionate, retinol, retinyl palmitate, retinyl acetate, retinal, retinoic acid, water-soluble vitamins, ascorbates, vitamin C, ascorbyl glucoside, ascorbyl palmitate, magnesium ascorbyl phosphate, sodium ascorbyl phosphate, vitamins and their salts and derivatives, provitamins and their salts and derivatives, ethyl panthenol, vitamin B and its derivatives, vitamin B1, vitamin B2, vitamin B6, vitamin B12, vitamin K and its derivatives, pantothenic acid and its derivatives, pantothenyl ethyl ether, panthenol and its derivatives, ethyl panthenol, dexpanthenol, biotin, amino acids and their salts and derivatives, water-soluble amino acids, asparagine, alanine, indol, glutamic acid, water-insoluble vitamins, vitamin A, vitamin E, vitamin F, vitamin D and its compounds, mono-, di-, and triterpenoids, beta-ionol, cedrol, and derivatives thereof, water-insoluble amino acids, tyrosine, tryptamine, particulate materials, butylated hydroxytoluene, butylated hydroxyanisole, allantoin, tocopherol nicotinate, tocopherol, tocopherol esters, palmitoyl-gly-his-lys, phytosterol, hydroxy acids, glycolic acid, lactic acid, lactobionic acid, keto acids, pyruvic acid, phytic acid, lysophosphatidic acid, stilbenes, cinnamates, resveratrol, kinetin, zeatin, dimethylaminoethanol, natural peptides, soy peptides, salts of acid sugars, manganese gluconate, zinc gluconate, piroctone olamine, 3,4,4'-trichlorocarbanilide, triclocarban, zinc pyrithione, hydroquinone, kojic acid, ascorbic acid, magnesium ascorbyl phosphate, ascorbyl glucoside, pyridoxine, aloe vera, terpene alcohols, allantoin, bisabolol, dipotassium glycyrrhizinate, glycerol acid, sorbitol, pentaerythritol, pyrrolidone and its salts, dihydroxyacetone, erythrulose, glyceraldehyde, tartaraldehyde, clove oil, menthol, camphor, eucalyptus oil, eugenol, menthyl lactate, witch hazel distillate, copolymer of eicosene and vinyl pyrrolidone, iodopropyl butylcarbamate, a polysaccharide, an essential fatty acid, a salicylate, glycyrrhetinic acid, carotenoids, ceramides and pseudo-ceramides, a complex lipid, oils in general of natural origin such as shea butter, apricot oil, evening primrose oil, prune oil, palm oil, monoi oil, kahai oil, hydroquinone, HEPES, procysteine, O-octanoyl-6-D-maltose, the disodium salt of methyl glycine diacetic acid, steroids such as diosgenin and DHEA derivatives, DHEA dehydroepiandrosterone and/or a chemical or biological precursor or derivative, N-ethylcarbonyl-4-para-aminophenol, bilberry extracts, phytohormones, *Saccharomyces cerevisiae* yeast extracts, seaweed extracts, extracts of soya, rapeseed, flax, spelt, rice, lupin, maize and/or peas, alverine and its salts, in particular alverine citrate, holly and horse chestnut extracts and combinations thereof, an inhibitor of metalloproteinases, and *Schinus molle* extracts.

Such additional ingredients may also be selected from the group comprising: peptides sold under the trade name MATRIXYL®, ARGIRELINE®, CHRONOGEN™, LAMINIXYL IS™ PEPTIDE Q10™, COLLAXYL™ (patent FR2827170), PEPTIDE VINCI 01™ (patent FR2837098), PEPTIDE VINCI 02™ (patent FR2841781), ATPeptide™ (patent FR2846883) or a peptide of sequence Arg-Gly-Ser-NH2, sold under the trade name ATPeptide™ by ASHLAND®, or an extract of *Artemia salina*, sold under the trade name GP4G™ (FR2817748), a yeast extract (Dynagen™, patent FR2951946 or Actopontine™ patent FR2944526).

In all cases, the person skilled in the art shall ensure that these adjuvants and their proportions are chosen in such a way as not to adversely affect the desired advantageous properties of the composition according to the invention.

Finally, a fourth object of the invention is the use of cosmetic compositions to reduce the signs of skin fatigue in a healthy person.

Signs of skin fatigue result from the combined effects of several factors related to lifestyle (eating habits, exposure to pollution), emotions (psychological stress, overwork) and lack of rest or poor quality sleep (Flament et al, How a working day-induced-tiredness may alter some facial signs in differently aged Caucasian women, Int J Cos Sci, 1-9, 2017). Clinically, the most common facial signs of skin fatigue are: puffiness and dark circles under the eyes, dull complexion, dry skin, accentuation of fine lines and wrinkles such as forehead or crow's feet wrinkles, and an accentuation of skin slackening; increased nail fragility, and reduced hairline have also been observed in healthy people in association with fatigue.

This application relates to care compositions and cosmetic care methods for healthy people.

At the molecular and cellular level, mitochondrial dysfunction has been associated with fatigue (Filler et al, Association of mitochondrial dysfunction and fatigue: a review of the literature, BBA Clinical, 1, 12-23, 2014). Indeed, mitochondria play a key role in the production of energy in the form of ATP. Maintaining the energy level in the cell is essential for cell synthesis, regeneration and division as well as protection and repair (Blatt et al, Stimulation of skin's energy metabolism provides multiple benefits for mature human skin, Biofactors 25, 179-185, 2005). Within the cell, energy can also be produced by extramitochondrial pathways such as glycolysis and the creatine kinase system. Glycolysis is a key metabolic pathway for proliferative cells such as skin keratinocytes. The enzyme 6-phosphofructo-2-kinase/fructose-2,6-biphosphatase 3 (PFKFB3) plays an important role in the regulation of glycolysis by catalysing the formation of fructose 2,6 biphosphate, the accumulation of which promotes the activity of phosphofructokinase 1, an enzyme playing a major limiting role in glycolysis (Amelio et al, p63 adjusts sugar taste of epidermal layers, J Invest Dermatol, 137, 1204-1206, 2017). PFKFB3 is required to maintain keratinocyte proliferative activity (Hamanaka et al, PFKFB3, a direct target of p63, is required for proliferation and inhibits differentiation in epidermal keratinocytes, J Invest Dermatol, 137, 1267-1276, 2017).

Creatine kinase is also a key enzyme in the cell's energy capacity. ATP is stored in the form of phosphocreatine, produced by the creatine kinase, which then allows its transport and availability in case of high energy demand (Lenz et al, The creatine kinase system in human skin: protective effects of creatine against oxidative and UV damage in vitro and in vivo, J Invest Dermatol, 124:443-452, 2005).

Thus, the invention has as its object the cosmetic use of a composition according to the invention for reducing the signs of fatigue that may appear in a healthy person, wherein the signs of fatigue of the skin are selected from: the presence of puffiness and dark circles under the eyes, dull complexion, dryness of the skin, accentuation of fine lines and wrinkles such as forehead or crow's feet wrinkles, accentuation of skin slackening, an increase in the fragility of the nails and a receding of the hair line, or all of these signs.

The invention further relates to the cosmetic use of a composition in which the signs of skin fatigue are manifested at molecular and cellular level by a decrease in the production of ATP, glycolysis and the creatine kinase system, the expression of type I collagen, the synthesis of PFKFB3, the level of messenger RNA (mRNA) of 11b-HSD2 and an increase in the level of messenger RNA (mRNA) of 11b-HSD1.

The invention further relates to the cosmetic use of a composition according to the invention for increasing the synthesis of cellular ATP, increasing the activity of creatine kinase, increasing the expression of type I collagen, increasing the synthesis of PFKFB3, decreasing the level of messenger RNA (mRNA) of 11b-HSD1 and increasing the level of messenger RNA (mRNA) of 11b-HSD2.

The invention and the advantages deriving therefrom will be better understood by reading the following description and the non-limiting embodiments, which are described in relation to the annexed figures, in which.

EXAMPLE 1: PREPARATION OF A PLANT EXTRACT FROM PULP AND SKIN POWDER OF THE SEEDED *MYRCIARIA DUBIA* FRUIT

The pulp and skin of the freshly seeded *Myrciaria dubia* fruit, 70% ripe, are placed for drying in a hot air tunnel system heated to 60° C. under humidity control. The resulting powder (200 g) is placed in a glass reactor, equipped with a stirring means and heating by means of a double jacket in the presence of a heat-transfer fluid.

The solvent used (3800 g) for maceration is a mixture of 60% 1,3-propanediol and 40% demineralised water.

The *Myrciaria dubia* pulp and skin powder is dispersed in the solvent for 2 hours at 30° C., then the mixture is separated on a decanter, centrifuged to remove the pellet, and the supernatant is recovered and filtered. After filtration, the supernatant is a 3220 g extract, in solvent medium 60% 1,3-propanediol and 40% water.

The extract thus obtained is called "E1 *Myrciaria* extract" in the following examples. This extract E1 contains 2.0% dry matter including itself (results expressed in relation to the dry matter (DM)):
- 35.3%/DM of organic acids, including malic acid, citric acid and total ascorbic acid (ascorbic acid and dehydroascorbic acid);
- 10.1%/DM of sugars, including glucose, fructose, sucrose and maltose;
- 1.8%/DM of minerals, including potassium, magnesium, calcium, sodium, manganese, zinc and iron; traces of peptides/proteins and traces of CA1 compounds;
- 1.5%/MS of polyphenols in ellagic and gallic form.

The dry extract described above is obtained by a gravimetric method based on the mass before and after evaporation of the solvent present in the liquid extract.

Total ascorbic acid (ascorbic acid+dehydroascorbic acid) was determined using an HPLC/external calibration method.

Citric and malic acids were determined by an HPLC/DEDL method by external calibration.

The total sugars were determined using an HPLC/DEDL method by external calibration.

The polyphenols were determined by HPLC/DAD by external calibration.

The minerals were assayed according to a method adapted from the NF EN ISO 11885 standard (the NF EN ISO 11885 method is an analytical method by ICP/OES).

List of Abbreviations:
HPLC: High-Performance Liquid Chromatography
DAD: Diode Array Detector
DEDL: Evaporative Light-Scattering Detector
ICP-OES: Inductively Coupled Plasma Optical Emission Spectrometry

EXAMPLE 2: EFFECT OF E1 *MYRCIARIA* EXTRACT ON THE SYNTHESIS OF ATP ON DERMAL FIBROBLAST CULTURES IN A TIRED CONDITION

The aim of this study is to determine the level of ATP synthesis on dermal fibroblast cultures "tired" by replications and a nutrient-poor medium. These cultures are treated with the E1 extract at 0.1% (volume/volume), i.e. diluted $\frac{1}{1000}$th in the culture medium.

Protocol: Dermal fibroblast cultures are "tired" by a number of replications (cells used between passes 15 and 20) and are fed with a nutrient-poor medium (without glucose) for 3 days. These cultures are treated with 0.1% E1 *Myrciaria* extract, from the second day of stress and for the remaining two days of stress, i.e. 48 hours of treatment. On the fourth day, an application of 0.1% E1 *Myrciaria* extract is carried out for 1 minute, and then the ATP is determined by luminescence (Abcam—ref: ab113849).

Figure 1:
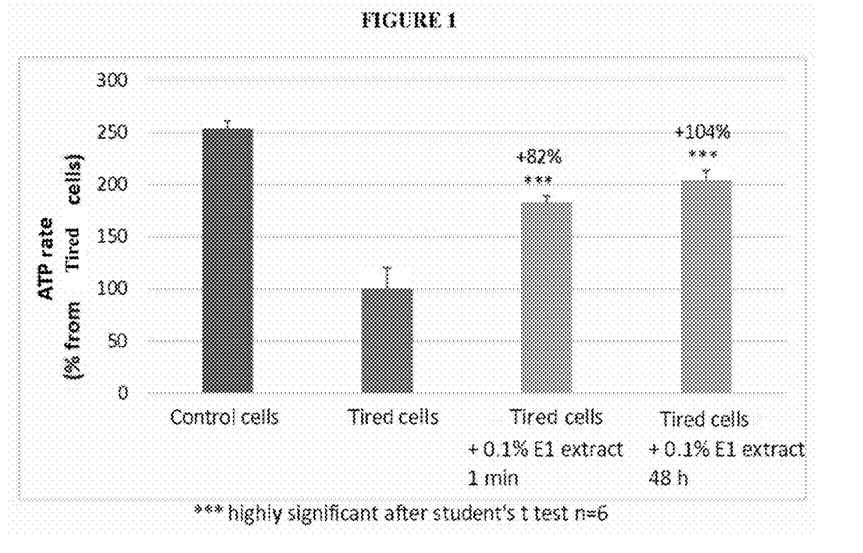
FIG. 1 shows the ATP measurement on dermal fibroblast cultures.

Results: After 48 hours of treatment with E1 *Myrciaria* extract, the ATP level is increased by +104% compared to untreated "tired" fibroblasts. After 1 min of treatment with E1 *Myrciaria* extract, the ATP level is increased by +82% compared to untreated "tired" fibroblasts. The results are shown in FIG. 1.

Conclusion: Treatment of "tired" fibroblasts with 0.1% E1 *Myrciaria* extract leads to an increase in ATP synthesis.

EXAMPLE 3: EFFECT OF E1 *MYRCIARIA* EXTRACT ON CREATINE KINASE ACTIVITY ON DERMAL FIBROBLAST CULTURES IN A TIRED CONDITION

The aim of this study is to determine the level of creatine kinase activity in dermal fibroblast cultures. The function of this enzyme is to catalyse the conversion of creatine to phosphocreatine, thus providing a rapidly usable energy reserve.

This activity measurement is performed on cultures of "tired" dermal fibroblasts treated with 0.1% E1 *Myrciaria* extract (volume/volume), i.e. diluted $\frac{1}{1000}$th in the culture medium.

Protocol: Dermal fibroblast cultures are "tired" by a few replications (cells used between passes 15 and 20) and are fed with a nutrient-poor medium (without glucose) for 3 days. These cultures are treated with 0.1% E1 *Myrciaria* extract, or with vitamin C at 4 µg/mL as a positive control, from the second day of stress and for the remaining two days of stress. Two days after the start of treatment, a measurement of creatine kinase activity is performed using a kit (Abcam—ref: ab155901).

For this purpose, the fibroblasts are detached with the CK buffer contained in the kit, recovered and centrifuged at 4000 g for 5 min at 4° C. The activity is then measured for each sample according to the kit protocol. Kinetics are obtained by a colorimetric reading with the Synergy 2 spectrometer (Biotek) coupled to Gen5 software.

Figure 2:
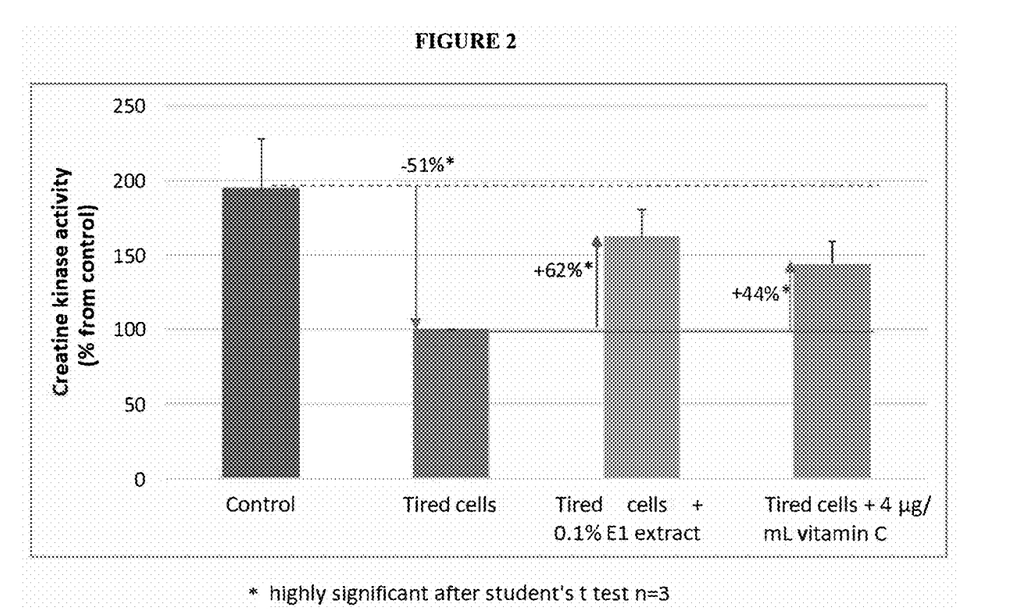
FIG. 2 shows the measurement of creatine kinase activity in dermal fibroblast cultures.

Results: In the condition where cells are "tired", creatine kinase activity decreases by −51%. With the treatment with 0.1% E1 *Myrciaria* extract, this enzymatic activity increases by +62% compared to untreated "tired" cells and by only +44% with the vitamin C treatment. The results are shown in FIG. 2.

Conclusion: The treatment of cells with 0.1% E1 *Myrciaria* extract prevents the decrease of creatine kinase activity on "tired" cells and is more important than the effect observed with vitamin C.

EXAMPLE 4: EFFECT OF E1 *MYRCIARIA* EXTRACT ON QPCR MEASUREMENT OF COL1A1 TYPE COLLAGEN ON RECONSTRUCTED DERMIS IN A "TIRED" CONDITION

The aim of this study is to determine the level of collagen I messenger RNA (mRNA) on equivalents of dermis reconstructed from fibroblasts tired by replications and a nutrient-poor environment. These cultures are treated with 0.1% E1 *Myrciaria* extract (volume/volume) i.e. diluted $\frac{1}{1000}$th in the culture medium.

Protocol: Dermal fibroblast cultures are "tired" by a number of replications (cells used between passes 15 and 20) and are fed with a nutrient-poor medium (without glucose) for two days. These cultures are also treated during these two days with 0.1% E1 *Myrciaria* extract (volume/volume), i.e. diluted $\frac{1}{1000}$th. A fibroblast culture (pass between 4 and 10) maintained in DMEM 1 g/L medium in glucose supplemented with 10% (v/v) foetal calf serum, 2 mM L-glutamine (Lonza) and 100 µg/mL Primocine (Invivogen), is used as a control.

From these fibroblast and collagen cultures, dermis equivalents are reconstituted. Once the reconstitution is done, the 0.1% E1 *Myrciaria* extract is added once at D0, D1 and D2. At D5 the dermis are frozen at −80° C.

The dermis are then thawed in order to extract the total RNAs.

To do this, the dermis are crushed using Gentle MACS (Mylteni) and the total RNAs extracted using the mirVana* miRNA Isolation Kit (AM1561, Ambion). The RNAs are then reverse-transcribed using the High Capacity cDNA Reverse Transcription Kit with RNase Inhibitor (4374966, Life technologies). Finally, the real-time PCR reaction is performed on a StepOnePlus thermal cycler (Applied Biosystems) with the TaqMan* Gene Expression Master Mix (4369514, Life technologies) and the TaqMan* Gene Expression Assays (Life technologies). The Ct (Threshold Cycle) comparison method is used for relative quantification of the targets, and the StepOne* software (Applied Biosystems) for data processing.

Figure 3:
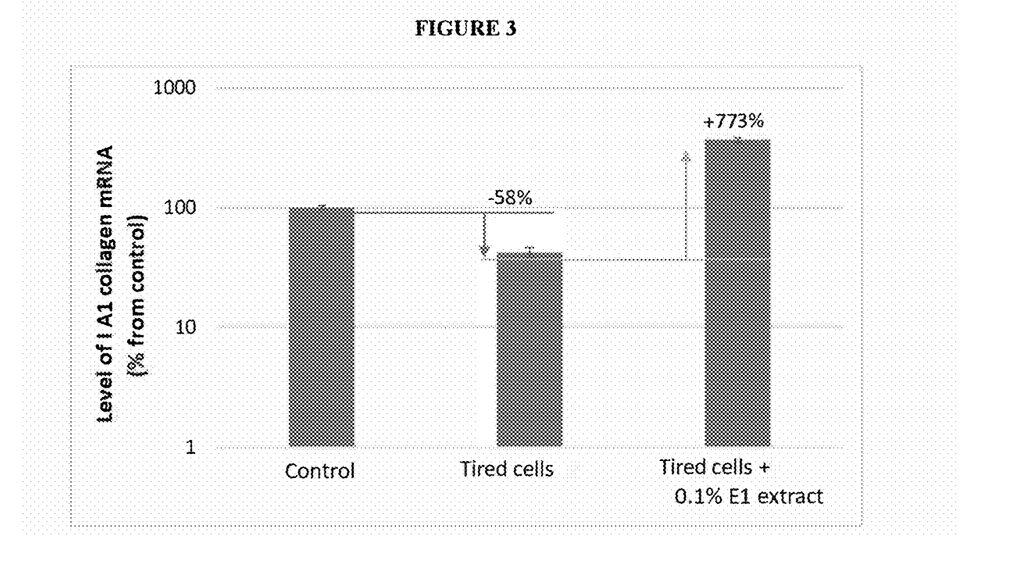
FIG. 3 shows the qPCR measurement of COL1A1 type collagen on reconstructed dermis.

Results: In the situation where the fibroblasts are "tired", the level of collagen I messenger RNA (mRNA) is decreased compared to non-tired fibroblasts by −58%. When these fibroblasts were cultured with the 0.1% E1 *Myrciaria* extract, the level of collagen I messenger RNA (mRNA) increases by +773%. The results are presented in FIG. 3.

Conclusion: The treatment of "tired" fibroblasts with 0.1% E1 *Myrciaria* extract, before and after reconstitution of equivalent dermis leads to an increase in messenger RNA (mRNA) of collagen I.

EXAMPLE 5: EFFECT OF E1 *MYRCIARIA* EXTRACT ON THE QPCR MEASUREMENT OF 11B-HSD1 AND 11B-HSD2 ON NORMAL HUMAN KERATINOCYTE (KHN) CULTURES

The aim of this study is to determine the messenger RNA (mRNA) level of 11b-HSD1 and 11b-HSD2 on keratinocytes. 11b-HSD enzymes catalyse the interconversion of active cortisol to inactive cortisone. Cortisol levels have been associated with anxiety and psychological stress, which may contribute to signs of skin fatigue. These cultures are treated with 0.1% E1 *Myrciaria* extract (volume/volume), i.e. diluted 1/1000th in the culture medium.

Protocol: Keratinocytes are cultured and treated with 0.1% E1 *Myrciaria* extract once daily for 24 hours and 48 hours. The messenger RNA (mRNA) levels of 11b-HSD1 and 11b-HSD2 are measured by real-time PCR.

To do this, total RNAs are extracted using the mirVana* miRNA Isolation Kit (AM1561, Ambion) and then reverse-transcribed using the High Capacity cDNA Reverse Transcription Kit with RNase Inhibitor (4374966, Life technologies). Finally, the real-time PCR reaction is performed on a StepOnePlus thermal cycler (Applied Biosystems) with the TaqMan* Gene Expression Master Mix (4369514, Life technologies) and the TaqMan* Gene Expression Assays (Life technologies). The Ct (Threshold Cycle) comparison method is used for relative quantification of the targets, and the StepOne* software (Applied Biosystems) for data processing.

Figure 4:
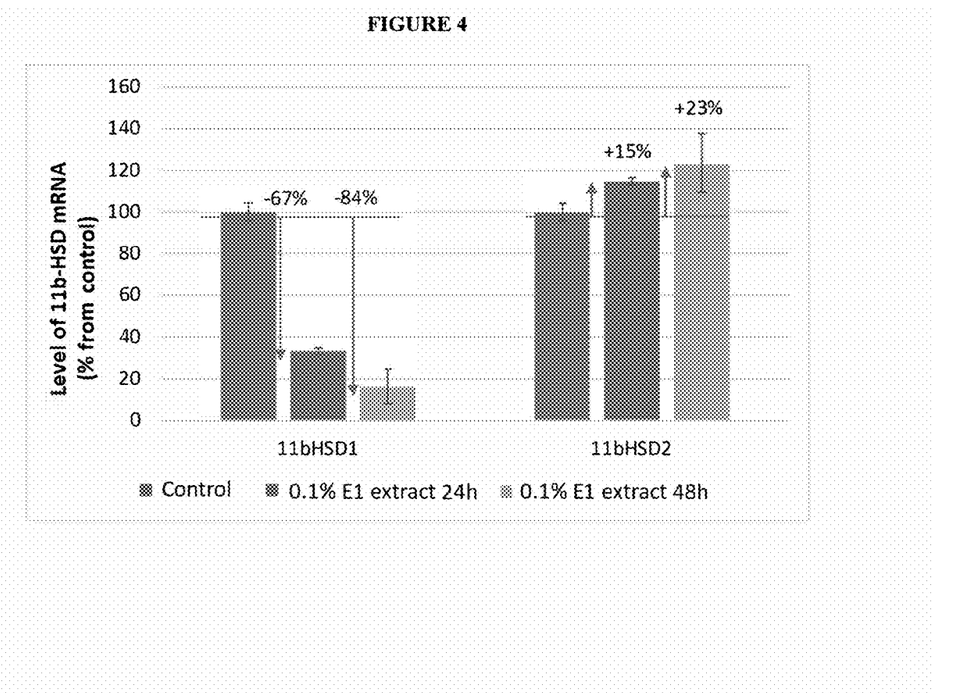
FIG. 4 shows the qPCR measurement of 11b-HSD1 and 11b-HSD2 in normal human keratinocyte (KHN) cultures.

Results: In KHN treated with E1 *Myrciaria* extract, the level of 11b-HSD1 decreased by −67% and −84% respectively after 24 and 48 hours of treatment. The level of 11b-HSD2 increased respectively by +15% and +23% after 24 and 48 hours of treatment. The results are shown in FIG. 4.

Conclusion: Treatment of keratinocytes with 0.1% E1 *Myrciaria* extract leads to a decrease in the level of 11b-HSD1 messenger RNA (mRNA) and an increase in the level of 11b-HSD2 messenger RNA (mRNA).

EXAMPLE 6: EFFECT OF E1 *MYRCIARIA* EXTRACT ON THE MORPHOLOGY OF RECONSTRUCTED EPIDERMIS IN A TIRED CONDITION

The aim of this study is to create a model of reconstructed "tired" human skin. To do this, the skin is reconstructed using adult donor keratinocytes and a respiratory chain inhibitor (rotenone) to create a lack of energy.

The use of a respiratory chain inhibitor such as rotenone creates mitochondrial dysfunction, including ATP depletion. Therefore, lack of cellular energy was equated in our model to a state of cellular fatigue (Han G et al, The mitochondrial complex I inhibitor rotenone induces endoplasmic reticulum stress and activation of GSK-3β in cultured rat retinal cells, Invest Ophthalmol Vis Sci. 31; 55(9):5616-28, 2014). These cultures are treated during the reconstruction with 0.1% E1 *Myrciaria* extract (volume/volume), i.e. diluted 1/1000th or 1% (volume/volume), i.e. diluted 1/100th in the culture medium.

Protocol: On day 12 of epidermal reconstruction, rotenone is added to the culture medium. A control condition is maintained without adding rotenone but changing the culture medium anyway. After 3 h incubation with the inhibitor, the medium is changed to a new medium containing 0.1% E1 *Myrciaria* extract and the epidermis is incubated again for 48 h. The placebo condition contains PBS (phosphate buffer saline) in the culture medium. The morphology of the skin is then observed by a Haematoxylin-Eosin (HE) staining.

For this, the reconstructed epidermises are fixed with formaldehyde and then embedded in paraffin. Cuts of 4 µm are then made.

For staining, the cuts are dewaxed by xylene and ethanol baths and then rinsed. Staining is done by a haematoxylin and then eosin bath.

The cuts are then examined under a microscope (Eclipse E600, Nikon) and photos are taken with the Q-capture acquisition software (QImaging*).

Figure 5:
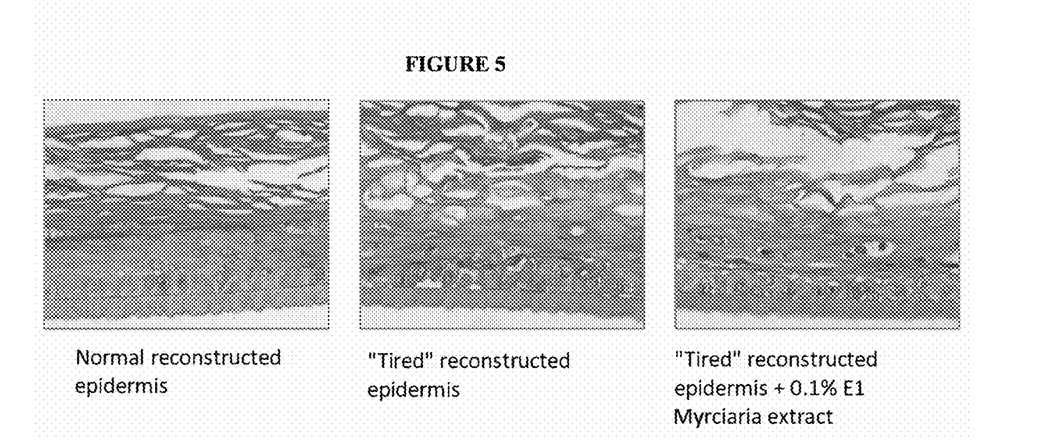
FIG. 5 shows the haematoxylin/eosin (HE) staining on reconstructed epidermis.

Results: In the condition where reconstructed epidermises are treated with rotenone, we observe a thinner epidermis than the control and a more damaged basal layer. When these are treated with 0.1% E1 *Myrciaria* extract, the epidermis seems to show less damage in its structure. The results are shown in FIG. 5.

Conclusion: Treatment of reconstructed epidermis with 0.1% E1 *Myrciaria* extract seems to partially compensate for the lack of energy induced by the inhibition of the respiratory chain by rotenone.

EXAMPLE 7: EFFECT OF E1 *MYRCIARIA* EXTRACT ON THE EXPRESSION OF PFKFB3 ON A RECONSTRUCTED EPIDERMIS IN A TIRED CONDITION

The aim of this study is to determine the level of expression of PFKFB3 (6-phosphofructo-2-kinase/fructose-2,6-biphosphatase 3) in a model of "tired" reconstructed human skin.

PFKFB3 is involved in the glycolysis process. It is an inducible enzyme that is expressed by the active epithelial cells of the epidermis. It enables the activation of the enzyme PFK-1 (phosphofructokinase-1), which limits this glycolysis process.

To obtain "tired" skin, this is reconstructed using adult donor keratinocytes and a respiratory chain inhibitor (rotenone) to create a lack of energy (see example 6). These cultures are treated during reconstruction with 0.1% E1 *Myrciaria* extract (volume/volume), i.e. diluted 1/1000th in the culture medium.

Protocol: On day 12 of epidermal reconstruction, rotenone is added to the culture medium. A control condition is maintained without adding rotenone but changing the culture medium anyway. After 3 h incubation with the inhibitor, the medium is changed to a new medium containing 0.1% E1 *Myrciaria* extract and the epidermises are incubated again for 48 h. The placebo condition contains PBS (phosphate buffer saline) in the culture medium. Detection of PFKFB3 expression is performed by an indirect immunofluorescence technique.

For this, the reconstructed epidermises are fixed with formaldehyde and then embedded in paraffin. Cuts of 4 µm are then made.

For staining, the cuts are dewaxed by xylene and ethanol baths and then rinsed. To unmask specific antigen binding sites, the cuts are heated in a citrate buffer bath in a microwave oven and then treated with a trypsin solution. After saturation with 5% BSA for 30 minutes to block non-specific sites, the cuts are then incubated with a PFKFB3 antibody solution for 1.5 hours and then with a solution of secondary anti-rabbit antibody coupled to a fluorochrome (Alexa Fluor® 488, Invitrogen) for 1 hour. The cuts are then examined under an Epi-fluorescence microscope (Zeiss Axiovert 200M microscope). A quantification of the fluorescence, using Volocity® image analysis software (PerkinElmer, Inc.), is performed from the obtained photographs.

Figure 6:
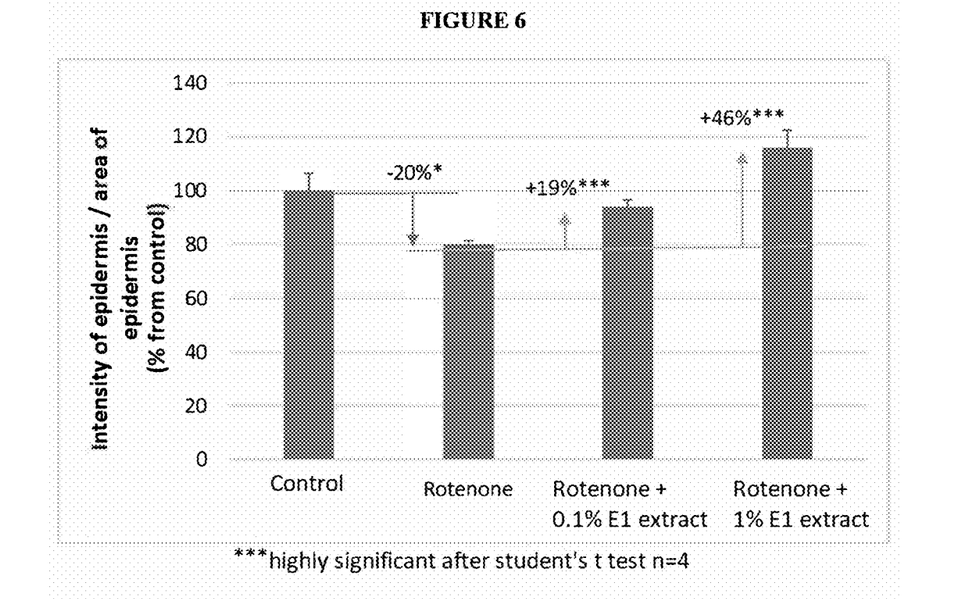
FIG. 6 shows the immunostaining intensity of PFKFB3 on reconstructed epidermis.

Results: In the condition where reconstructed epidermises are treated with rotenone, we observe a decrease in PFKFB3 expression of −20% compared to unstressed epidermises. When these are treated with 0.1% or 1% E1 *Myrciaria* extract, its expression increases by +19% and +46% respectively. The results are shown in FIG. 6.

Conclusion: Reconstructed epidermises treated with rotenone show a decrease in PFKFB3, reflecting reduced glycolysis. Treatment of these "tired" reconstructed epidermis with 0.1% E1 *Myrciaria* extract seems to partially compensate for this lack of energy observed by stimulating PFKFB3 synthesis.

EXAMPLE 8: EFFECT OF E1 *MYRCIARIA* EXTRACT ON THE ACTIVITY OF CREATINE KINASE ON A RECONSTRUCTED EPIDERMIS IN A TIRED CONDITION

The aim of this study is to determine the level of creatine kinase activity in a model of reconstructed human skin. The function of this enzyme is to catalyse the conversion of creatine to phosphocreatine, thus providing a rapidly usable energy reservoir.

This measure of activity is done on a model of "tired" reconstructed human skin obtained using adult donor keratinocytes and a respiratory chain inhibitor (rotenone) to create a lack of energy. These cultures are treated during reconstruction with 0.1% *Myrciaria* extract (volume/volume), i.e. diluted 1/1000th in the culture medium.

Protocol: On day 12 of epidermal reconstruction, rotenone is added to the culture medium. A control condition is maintained without adding rotenone but changing the culture medium anyway. After 3 h incubation with the inhibitor, the medium is changed to a new medium containing 0.1% E1 *Myrciaria* extract and the epidermises are incubated again for 48 h. The placebo condition contains PBS (phosphate buffer saline) in the culture medium. A measurement of creatine kinase activity is performed using a kit (Abcam—ref: ab155901).

To do this, the reconstructed epidermises are crushed using a glass pestle with the CK buffer contained in the kit, recovered, and centrifuged at 4,000 g for 5 min at 4° C. The activity is then measured for each sample according to the kit protocol. Kinetics are obtained by a colorimetric reading with the Synergy 2 spectrometer (Biotek) coupled with the to Gen5 software.

Figure 7:
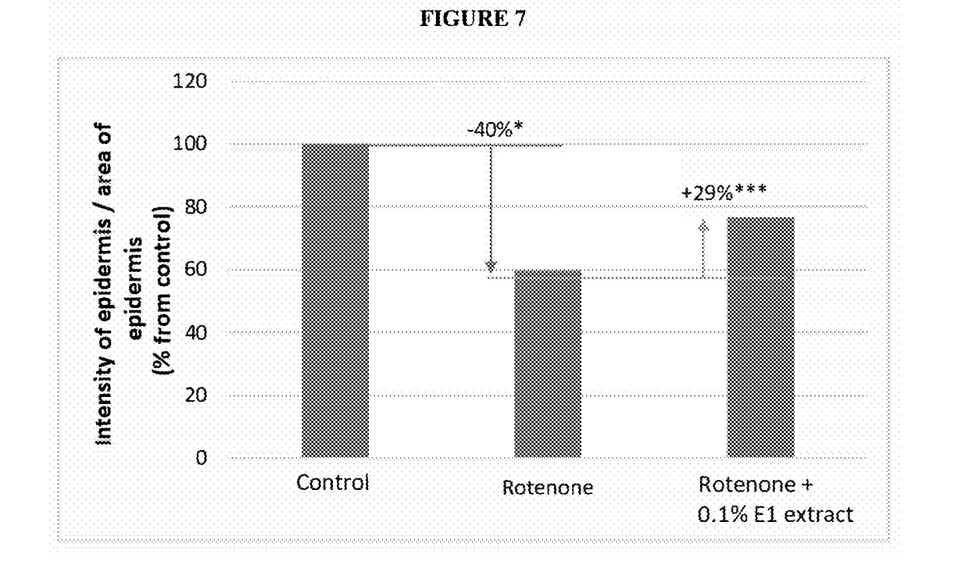
FIG. 7 shows the measurement of creatine kinase activity on reconstructed epidermis.

Results: In the condition where reconstructed epidermises are "tired", creatine kinase activity decreases by −40% compared to non-"tired" epidermises. With treatment with 0.1% E1 *Myrciaria* extract, this enzymatic activity increases by +29% compared to the "tired" model. The results are shown in FIG. 7.

Conclusion: The treatment of reconstructed epidermises with 0.1% E1 *Myrciaria* extract prevents the decrease in creatine kinase activity observed on a model of "tired" reconstructed skin.

EXAMPLE 9: VELVET CREAM FORMULATION

| Ingredient/Trade name | INCI name | % |
| --- | --- | --- |
| Phase A | | |
| Purified water | Water | 70.48 |
| Phase B | | |
| Natrosol ™ Plus 330 CS | Cetyl Hydroxyethylcellulose | 0.50 |
| Solagum AX* | Acacia Senegal Gum & Xanthan Gum | 1.00 |
| Phase C | | |
| Simulgreen 18-2* | Hydroxystearyl Alcohol & Hydroxystearyl Glucoside | 3.00 |
| Phase D | | |
| Ceraphyl ™ 791 ester | Isocetyl Stearoyl Stearate | 5.00 |
| Macadamia Nut Oil CP RBD | Macadamia Ternifolia Seed Oil | 5.00 |
| Virgin Prunus Oil | Prunus Domestica Seed Extract | 2.00 |
| Orchid ™ Complex OS ester | Caprylic/Capric Triglyceride (and) *Cymbidium Grandiflorum* Flower Extract | 5.00 |
| Phase E | | |
| Optiphen ™ BSB-N preservative | Benzyl Alcohol (and) Glycerin (and) Benzoic Acid (and) Sorbic Acid | 1.00 |
| Zemea* | Propanediol | 5.00 |
| Phase F | | |
| Extract E1 | 1,3-Propanediol (and) Water/Aqua (and) *Myrciaria Dubia* Fruit Extract | 1.00 |
| Phase G | | |
| Purified water | Water | 1.00 |
| Sodium Hydroxide | | 0.02 |

Method of Preparation:
1. In the main beaker, add the water and begin to homogenise by heating to 70-75° C.
2. Sprinkle in Natrosol Plus 330 CS and mix well for 30 minutes.
3. Sprinkle in Solagum AX and mix well for 20 minutes.
4. Add the phase ingredients to a second beaker and heat to 70-75° C.
5. Add phase C to phase A while homogenising.
6. At 70-75° C., add phase D to the main beaker and mix well. The emulsion should be homogeneous.
7. Start cooling down. Add phase E ingredients one by one at 50° C., mixing well after each addition.
8. At 25° C., add phase F and homogenise.
9. Premix phase G until a clear and uniform mixture is obtained. Add to the main beaker and mix well.
10. Stop at 25° C.
11. Appearance: White emulsion; opaque. pH: 4.4-4.8; viscosity (D0): 12000-20000 cps (Brookfield RVT/Spindle B/5 RPM/1 minute/25° C.)
12. The preservation of the formula was validated by a double test of effectiveness after 28 days. However, the preservatives were not optimised at their lowest level of effectiveness.

EXAMPLE 10: VITAFRUIT CREAM GEL FORMULATION

Method of Preparation:
1. In the main beaker add the ingredients of phase A, one by one, heating to 70° C. while mixing until completely homogenised.
2. Sprinkle in the polymer FlexiThix™ and homogenise until a smooth mixture is obtained.
3. In a separate beaker, heat phase C (except Antaron™/Ganex™ Sensory polymer) to 70° C. until homogenised. Then immerse the Antaron/Ganex Sensory polymer in phase C under stirring.
4. At 70° C., add phase C (Antaron/Ganex Sensory polymer are in wet powder form) to the main beaker and homogenise.
5. Cool.
6. At 25° C., add phase D slowly and mix until completely homogenised.
7. Add phase E and mix until completely homogenised (viscosity increases).
8. At room temperature, pre-mix phase F with stirring, add the contents of the main beaker and mix well.
9. Stop when mixture is uniform in colour.
10. Appearance: orange opalescent cream gel; pH: 6.0-6.5; viscosity (D0): 25000-40000 cps (Brookfield RVT/Spindle B/5 RPM/1 minute/25° C.).
11. The preservation of the formula was validated by a 3-month accelerated ageing test and an efficacy test

| Ingredient/Trade name | INCI name | % |
| --- | --- | --- |
| Phase A | | |
| Purified water | Water/Aqua | Qs. 100 |
| Tetrasodium EDTA | Tetrasodium EDTA | 0.05 |
| Lubrajel ™ Oil Free hydrogel* | Glycerin (and) Glyceryl Acrylate/Acrylic Acid Copolymer (and) PVM/MA Copolymer | 7.00 |
| Optiphen ™ HD preservative booster | 1,2-Hexanediol | 3.00 |
| Butylene Glycol | Butylene Glycol | 7.00 |
| Glycerol | Glycerin | 5.00 |
| Phase B | | |
| FlexiThix ™ polymer | PVP | 2.00 |
| Phase C | | |
| Montanov ™ 68* | Cetearyl Alcohol (and) Cetearyl Glucoside | 0.20 |
| Optiphen 200 condom | Phenoxyethanol (and) Caprylyl Glycol | 0.90 |
| Ceraphyl ™ SLK ester | Isodecyl Neopentanoate | 2.50 |
| Lexfeel ™ N5* | Diheptyl Succinate (and) Capryloyl Glycerin/Sebacic Copolymer | 1.00 |
| Ganex ™/Ganex ™ Sensory polymer | VP/Acrylates/Lauryl Methacrylate Copolymer | 0.25 |
| Phase D | | |
| Surfin ™ 96* | Alcohol | 10.00 |
| Phase E | | |
| RapiThix ™ A-60 polymer | Sodium Polyacrylate (and) Hydrogenated Polydecene (and) Trideceth-6 | 0.50 |
| Phase F | | |
| Extract E1 | 1,3-Propanediol (and) Water/Aqua (and) *Myrciaria Dubia* Fruit Extract | 1.00 |
| Phase A | | |
| Smart 5* | Isododecane (and) Hydrogenated Tetradecenyl/Methylpentadecene | 5.00 |
| Unicert Yellow 08005-J (Sol. 1%) | CI 19140 (yellow 5) | 0.35 |
| Unicert Red 07004-J (sol. 1%) | CI 14700 (red 4) | 0.25 |
| Timiron ™ Silk Gold * | CI 77891 (Titanium Dioxide) (and) Mica (and) Tin Oxide | 1.00 |
| PF Caipirinha Fresh G11724962 | Fragrance/Parfum (and) Benzyl Salicylate (and) Citral (and) Limonene (and) Linalool (and) Butylphenyl methylpropional (Filial) | 0.30 | after 28 days. However, the preservatives were not optimised at their lowest level of effectiveness.

BIBLIOGRAPHICAL REFERENCES (1) Myoda, T.; Fujimura, S.; Park, B.; Nagashima, T.; Nakagawa, J.; Nishizawa, M. *Int. J. Food Agric. Environ.* 2010, 8 (2), 304.
(2) Yazawa, K.; Suga, K.; Honma, A.; Shirosaki, M.; Koyama, T. *J. Nutr. Sci. Vitaminol.* (*Tokyo*) 2011, 57 (1), 104.
(3) Kaneshima, T.; Myoda, T.; Toeda, K.; Fujimori, T.; Nishizawa, M. *Biosci. Biotechnol. Biochem.* 2017, 81 (8), 1461.
(4) Fracassetti, D.; Costa, C.; Moulay, L.; Tomás-Barberán, F. A. *Food Chem.* 2013, 139 (1-4), 578.
(5) Zanatta, C. F.; Mercadante, A. Z. *Food Chem.* 2007, 101 (4), 1526.
(6) Zanatta, C. F.; Cuevas, E.; Bobbio, F. O.; Winterhalter, P.; Mercadante, A. Z. *J. Agric. Food Chem.* 2005, 53 (24), 9531.
(7) Akter, M. S.; Oh, S.; Eun, J.-B.; Ahmed, M. *Food Res. Int.* 2011, 44 (7), 1728.
(8) Justi, K. C.; Visentainer, J. V.; Evelazio de Souza, N.; Matsushita, M. *Arch. Latinoam. Nutr.* 2000, 50 (4), 405.
(9) Zapata, S. M.; Dufour, J.-P. *J. Sci. Food Agric.* 1993, 61 (3), 349.

The invention claimed is:

1. A process for obtaining an extract, the method comprising:
providing pulp and skin of the seed-free dried fruit of *Myrciaria dubia*, having a ripeness of at least 70% and a soluble solids/acidity ratio of 2.5 to 3;
dispersing and extracting the pulp and skin of the seed-free dried fruit in a hydro-polyalcohol solvent;
separating a liquid phase loaded with compounds of interest from the solid phase of the pulp and skin of the seed-free dried fruit and hydro-polyalcohol dispersion; and
microfiltering the liquid phase to remove solid plant particles.

2. The process according to claim 1, wherein the hydro-polyalcohol solvent is a mixture comprising from 10% to 90% by weight of glycerol and/or 1,3-propanediol in demineralised water in relation to the total weight of solvent plus water.

3. The process according to claim 2, wherein extracting is a solid-liquid extraction with a hydro-glycolic solvent composed of 60% 1,3-propanediol and 40% demineralised water.

4. The process according to claim 1, wherein extracting is carried out at a temperature between 4° C. and 100° C. for a time between 10 minutes and 4 hours stirring or with ultrasound.

5. The method according to claim 1, wherein separating comprises decanting and/or centrifuging.

6. The method according to claim 1, wherein separating comprises clarifying filtering.

7. The method according to claim 1, wherein, after microfiltering the liquid phase, the liquid phase is purified by ultrafiltration and/or nanofiltration.

8. The method according to claim 1, comprising drying the extract by spraying, freeze-drying, or zeodration.

* * * * *